United States Patent
Novak et al.

(10) Patent No.: US 10,806,372 B2
(45) Date of Patent: Oct. 20, 2020

(54) METHOD AND SYSTEM FOR SIMULTANEOUS EVALUATION OF AIRWAY WALL DENSITY AND AIRWAY WALL INFLAMMATION

(71) Applicant: Siemens Healthcare GmbH, Erlangen (DE)

(72) Inventors: Carol L. Novak, Newtown, PA (US); Benjamin L. Odry, West New York, NJ (US); Atilla Peter Kiraly, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 1013 days.

(21) Appl. No.: 14/840,357

(22) Filed: Aug. 31, 2015

(65) Prior Publication Data

US 2017/0055876 A1 Mar. 2, 2017

(51) Int. Cl.
*A61B 5/08* (2006.01)
*A61B 5/087* (2006.01)
(Continued)

(52) U.S. Cl.
CPC ............ *A61B 5/0813* (2013.01); *A61B 5/087* (2013.01); *A61B 6/032* (2013.01); *A61B 6/463* (2013.01);
(Continued)

(58) Field of Classification Search
CPC ....... A61B 5/0813; A61B 6/481; A61B 5/087; A61B 6/50; A61B 6/5217; A61B 6/463;
(Continued)

(56) References Cited

U.S. PATENT DOCUMENTS 6,813,333 B2 * 11/2004 Karau .................... A61B 6/032
378/19
8,605,978 B2 * 12/2013 Mizuno ................ G06T 7/0012
382/128
(Continued)

OTHER PUBLICATIONS

Kiraly A.P., Helferty J.P., Hoffman E.A., McLennan G., and Higgins W.E., "Three-Dimensional Path Planning for Virtual Bronchoscopy", In IEEE Transactions on Medical Imaging, vol. 23, No. 1, Nov. 2004: p. 1365-1379.
(Continued)

*Primary Examiner* — Baisakhi Roy (57) ABSTRACT

A method of evaluating airway wall density and inflammation including: segmenting a bronchial tree to create an airway wall map; for each branch, taking a set of locations that form the wall of each branch from the map and sampling the value in a virtual non-contrast image of the bronchial tree and, given a set of samples of pre-contrast densities, computing a value to yield a bronchial wall density for each branch to yield density measures; for each branch, taking the set of locations that form the wall of each branch from the map and sampling the value in a contrast agent map of the bronchial tree and, given the set of samples of contrast agent intake, computing a value to yield a bronchial wall uptake for each branch to yield inflammation measures; and using the density and inflammation measures to determine treatment or predict outcome for a patient.

9 Claims, 7 Drawing Sheets

(51) Int. Cl.
    A61B 6/03      (2006.01)
    A61M 5/00      (2006.01)
    A61B 6/00      (2006.01)
(52) U.S. Cl.
    CPC .............. *A61B 6/481* (2013.01); *A61B 6/50*
            (2013.01); *A61B 6/5217* (2013.01); *A61M*
        *5/007* (2013.01); *A61B 6/482* (2013.01); *A61B*
                                    *2576/00* (2013.01)
(58) Field of Classification Search
    CPC ......... A61B 6/032; A61B 6/482; A61B 6/507;
                    A61B 2576/00; A61M 5/007; G06T
                                            2207/30061
    See application file for complete search history.

(56)                References Cited

U.S. PATENT DOCUMENTS 9,773,311 B2*   9/2017  Ross .................... G06T 7/136
 2005/0105788 A1*   5/2005  Turek .................. G06F 19/321
                                                        382/131
 2012/0268450 A1   10/2012  Kiraly et al.
 2012/0288173 A1   11/2012  Rai et al.
 2013/0261441 A1*  10/2013  Das ..................... A61B 6/481
                                                        600/431
 2015/0265184 A1*   9/2015  Wondka ................ A61B 5/097
                                                        600/532

OTHER PUBLICATIONS

B. Odry, A. P. Kiraly, G. Slabaugh, C. L. Novak, "Active contour approach for accurate quantitative airway analysis", SPIE Medical Imaging 2008, Proceedings of the SPIE vol. 6916, p. 691613, 2008.

Odry, B, Naidich, D, Barreto, M, Giusti, R, Krauss, B, Kiraly, A, Novak, C, Schmidt, B, "Quantitative Dual-Energy CT Evaluation of Bronchial Wall Enhancement: A Feasibility Study Using Phantoms and Cystic Fibrosis Patients." Radiological Society of North America 2011 Scientific Assembly and Annual Meeting, Nov. 26-Dec. 2, 2011 ,Chicago IL.
Sonya Koo, MD, PhD, and Andrew Yen, MD, "High attenuation in the lungs on CT: Beyond calcified granulomas", Applied Radiology, Mar. 4, 2013.
Kiraly A.P., McLennan G., Hoffman E.A., Reinhardt J.M., and Higgins W.E., "Three-dimensional human airway segmentation methods for clinical virtual bronchoscopy", Academic Radiology, 2002. 9(10): p. 1153-1168.
Fetita C.I., Preteux F., Beigelman-Aubry C., and Grenier P., (2004) "Pulmonary airways: 3-D reconstruction from multislice CT and clinical investigation," vol. 23, No. 11, IEEE Trans. Medical Imaging, Nov. 2004.
A. P. Kiraly, B. L. Odry, D. P. Naidich, C. L. Novak, "Boundary-Specific Cost Functions for Quantitative Airway Analysis", Medical Image Computing and Computer Assisted Intervention (MICCAI) 2007, p. 784-791.
"Lung lobe segmentation by anatomy-guided 3D watershed transform," Jan-Martin Kuhnigk, Horst K. Hahn, Milo Hindennach, Volker Dicken, Stefan Krass, and Heinz-Otto Peitgen, Proceedings of the SPIE, vol. 5032, p. 1482-1490 (2003).
B L. Odry; A P. Kiraly; C L. Novak; D P. Naidich; J-F Lerallut "Automated airway evaluation system for multi-slice computed tomography using airway lumen diameter, airway wall thickness and broncho-arterial ratio" Proc. SPIE 6143 Medical Imaging 2006, 61430Q.
B. L. Odry; D. Guiliguian; A. P. Kiraly; C. L. Novak; D. P. Naidich; JF Lerallut, "Automated detection of mucus plugs within bronchial tree in MSCT images" Proc. SPIE 6511 Medical Imaging 2007, 651110.

* cited by examiner

METHOD AND SYSTEM FOR SIMULTANEOUS EVALUATION OF AIRWAY WALL DENSITY AND AIRWAY WALL INFLAMMATION

CROSS-REFERENCE TO RELATED APPLICATIONS

This application claims priority to U.S. provisional application No. 62/047,685, filed Sep. 9, 2014, U.S. provisional application No. 62/047,814, filed Sep. 9, 2014, U.S. provisional application No. 62/047,994, filed Sep. 9, 2014, and U.S. provisional application No. 62/048,605, filed Sep. 10, 2014, the disclosures of which are incorporated by reference herein in their entireties.

TECHNICAL FIELD

The present invention relates to the analysis of airways in medical images.

DISCUSSION OF THE RELATED ART

Pulmonary diseases such as bronchiectasis, asthma, cystic fibrosis and Chronic Obstructive Pulmonary Disease (COPD) are characterized by abnormalities in airway dimensions, including the thickness of the walls and the size of the lumen (e.g., an inner airway). Computed Tomography (CT) has become one of the primary means to depict and detect these abnormalities, as the availability of high-resolution near-isotropic data makes it possible to evaluate airways at oblique angles to the scanner plane. However, currently, clinical evaluation of airways is typically limited to subjective visual inspection. Systematic evaluation of the airways to take advantage of high-resolution data has not proved practical without automation.

Recently, automated methods have been proposed based on the automatic extraction and modeling of the airway tree. Such a model captures the geometry and the hierarchy of the airway tree structure. These methods create the model by a combination of segmentation and the creation of a tree structure from the segmentation. An example of one such method is found in Kiraly A. P., Helferty J. P., Hoffman E. A., McLennan G., and Higgins W. E., "Three-Dimensional Path Planning for Virtual Bronchoscopy", In IEEE Transactions on Medical Imaging, vol. 23, no. 1, November 2004: p. 1365-1379. After an airway tree model is obtained, measurements of the airway dimensions, including wall thickness are performed. An example of this is described in B. Odry, A. P. Kiraly, G. Slabaugh, C. L. Novak, "Active contour approach for accurate quantitative airway analysis", SPIE Medical Imaging 2008, Proceedings of the SPIE Vol. 6916, p. 691613, 2008. Once airway measurements have been obtained, they can be classified into normal or abnormal. The results can be colored directly on the model to depict normal and abnormal bronchi, or to depict severity.

However, airway walls may be thicker due to inflammatory disease process or to other processes such as scarring. Furthermore, inflammatory causes of thickening may be potentially treatable (such as with anti-inflammatory agents) whereas scarring type processes are less likely to respond to treatment. Hence, it would be valuable to know whether observed wall thickening is due to an inflammatory process, to better individualize patient treatment.

It has been shown that the airway walls of certain patients with airway disease experience increases in apparent density following the administration of iodinated contrast. It has also been shown that the amount of iodine uptake may be estimated with Dual Energy Computed Tomography (DECT) imaging. Such an example is described in Odry, B, Naidich, D, Barreto, M, Giusti, R, Krauss, B, Kiraly, A, Novak, C, Schmidt, B, "Quantitative Dual-Energy CT Evaluation of Bronchial Wall Enhancement: A Feasibility Study Using Phantoms and Cystic Fibrosis Patients." Radiological Society of North America 2011 Scientific Assembly and Annual Meeting, Nov. 26-Dec. 2, 2011, Chicago Ill. The result of DECT imaging is an iodine map that depicts the amount of iodine uptake at any given location in the volume.

However, airway walls may also show differing densities when no contrast agent is given. Such a case is described in Sonya Koo, MD, PhD, and Andrew Yen, MD, "High attenuation in the lungs on CT: Beyond calcified granulomas", Applied Radiology, Mar. 4, 2013. These differing densities may be due to calcification of airway wall tissues due to repeated injury to the tissue, such as that caused by cigarette smoking or other irritants. These changes in the base tissue density may be a significant marker of disease.

SUMMARY OF THE INVENTION

According to an exemplary embodiment of the present invention, a method of evaluating airway wall density and airway wall inflammation includes: segmenting a bronchial tree, from image data for a patient, to create an airway wall map that indicates for each element in the airway wall map whether it is part of an airway or not; for each branch or set of branches, taking a set of locations that form the wall of each branch from the airway wall map and sampling the value in a virtual non-contrast image of the bronchial tree to determine pre-contrast density and, given the set of samples of pre-contrast densities, computing a value to yield a bronchial wall density for each branch to yield density measures; for each branch or set of branches, taking the set of locations that form the wall of each branch from the airway wall map and sampling the value in a contrast agent map of the bronchial tree to determine contrast agent intake and, given the set of samples of contrast agent intake, computing a value to yield a bronchial wall uptake for each branch to yield inflammation measures; and using the density measures and inflammation measures to determine treatment or predict outcome for the patient.

The contrast agent map shows for every voxel, the computed amount contrast agent present at the corresponding location in the patient's body.

The method further includes visualizing wall density or inflammation in the bronchial tree.

The wall density or inflammation is color coded on the rendered bronchial tree.

The contrast agent includes iodine.

According to an exemplary embodiment of the present invention, a method of assessing airflow in the lungs includes: receiving a high-resolution image; detecting, in a hierarchical structure of a bronchial tree from the high-resolution image, a generation where airway restriction is located, and using the generation to determine a number of children branches that are potentially impacted by the airway restriction; computing an estimated impacted volume using a ratio between a value representative of the number of children branches that are potentially impacted by the airway restriction and a predetermined maximum number of airways; and presenting, on a display device, the estimated impacted volume.

The airway restriction is due to mucoid impaction.

The estimated impacted volume presented on the display device starts from an impacted parent airway and follows contours of the impacted airway's tree beyond the start point.

Color coding depicts a percentage of impacted volume compared to a total lobe volume.

Different colors are indicative of abnormalities of a particular extent and severity. The percentage of impacted volume is associated with a scoring system to map percentages to different colors.

The estimated impacted volume is further computed by using a bronchial lumen to artery (BLA) or a bronchial wall thickness to artery diameter (BWA) ratio.

The value representative of the number of children branches that are potentially impacted is a sum of all airways when the predetermined maximum number of airways is determined considering all of the airways individually using a BLA or a BWA ratio.

According to an exemplary embodiment of the present invention, a method of reduction of partial volume effects for visualization of iodine in airway walls includes: computing a first volume map from a computed tomography (CT) volume in image data of a patient to determine which voxels of the CT volume are included in vessels; computing a second volume map from the CT volume to determine which voxels of the CT volume are not included in the vessels; using the second volume map and an iodine map to produce a map of iodine outside the vessels; visualizing a multi-planar reconstruction (MPR) of gray-scale data of the CT volume with the iodine map and the map of iodine outside the vessels overlaid on the MPR; and interpolating data of the visualized overlay from the map of iodine outside the vessels.

The first volume map is the result of an automatic vessel segmentation.

The automatic vessel segmentation performs additional dilation steps to capture edges of the vessels in the first volume map.

The second volume map is computed by taking the logical not of the first volume map.

The map of iodine outside the vessels is produced by taking the logical and of the second volume map and the iodine map.

The visualized overlay includes a color lookup table that depicts different amounts of iodine as different hues.

The visualized overlay includes an alpha blending function.

According to an exemplary embodiment of the present invention, a method for presentation of airway abnormalities from CT includes: segmenting a bronchial tree of a patient; computing iodine uptake in a wall of each branch of the tree, wherein the result for each branch is an estimate of the iodine update; and using the estimated iodine uptake of a particular branch to determine a degree of inflammation in that branch.

The method further includes ordering branches in the bronchial tree from most abnormal to least abnormal by using a BLA or a BWA ratio.

The method further includes sorting lumen diameter by generation or size.

The method further includes sorting wall thicknesses by generation.

The method further includes sorting inflammation values of the iodine map from most iodine uptake to least iodine uptake.

The method further includes displaying abnormal branches according to user selected criteria.

The method further includes displaying a magnified view of an abnormal airway with an MPR perpendicular to the airway's axis to show the airway's cross-section.

The method further includes overlaying inner and outer wall contours on a displayed abnormal airway to show how the airway was computed.

DETAILED DESCRIPTION OF EXEMPLARY EMBODIMENTS

An exemplary embodiment of the present invention provides a method for simultaneously estimating the density of airway walls prior to the administration of contrast and the density increase following iodine administration. It is to be understood that this automated evaluation occurs after the contrast is given to the patient. The combination of these two measurements provides valuable information for diagnosis as well as for recommending therapy and evaluating its effectiveness.

Figure 1:
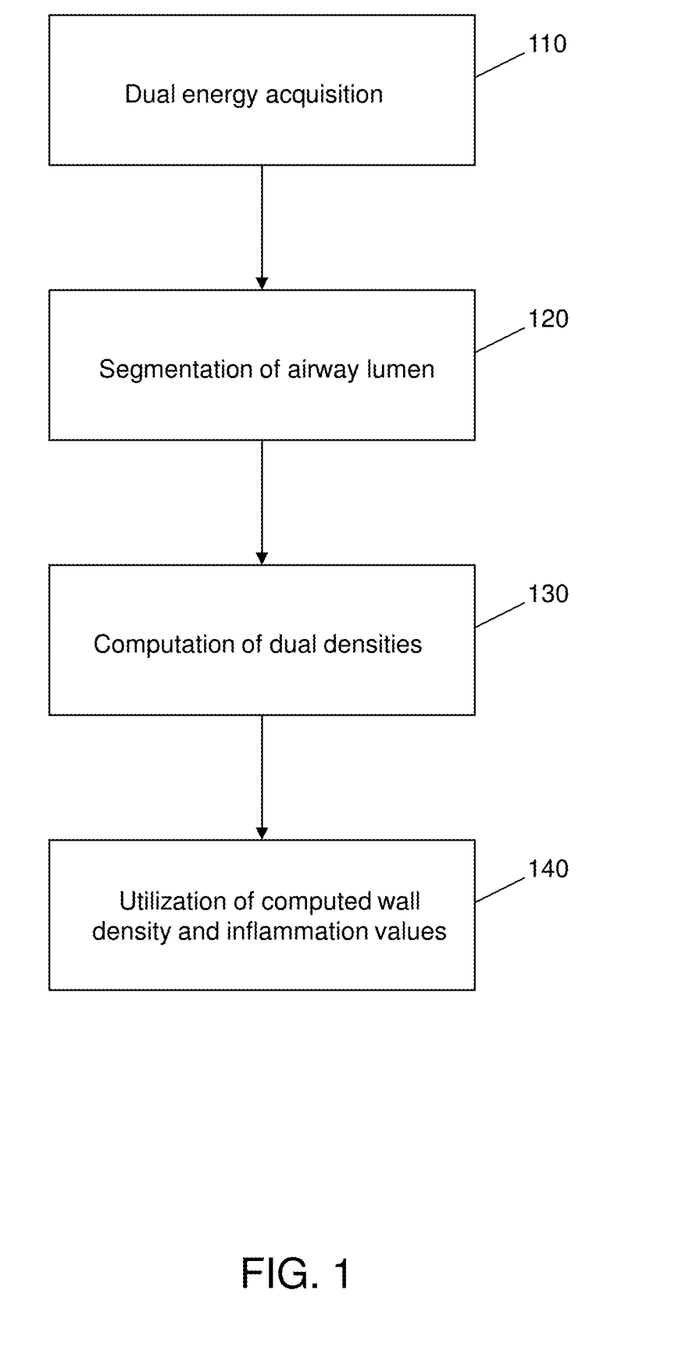
FIG. 1 is a flowchart of a method for simultaneous evaluation of airway wall density and airway wall inflammation according to an exemplary embodiment of the present invention.

Included in the method for simultaneously estimating the density of airway walls prior to the administration of contrast and the density increase following iodine administration, is a step of dual energy acquisition 110 (see FIG. 1). It is to be understood that dual energy acquisition involves acquiring CT volumes after injecting a contrast agent, and not before injection, so there would be no pre-contrast image available, only a virtual non-contrast image that is computed from the dual energy volumes. The use of a virtual non-contrast image saves the radiation dose that would be needed to acquire true pre-contrast images. Simultaneous acquisition of dual energy volumes also eliminates the registration problem of matching pre- and post-contrast images.

For example, the dual energy acquisition produces two volumes, one at low energy (e.g., 80 kV) and one at high energy (e.g., 140 kV or 150 kV). These volumes may be referred to as $V_{low}$ and $V_{high}$. A computer with a Dual Energy software module may be used to create a volume that simulates an acquisition at an average energy $V_{average}$ (e.g., 120 kV), by taking a weighted average of $V_{low}$ and $V_{high}$.

Figure 2:
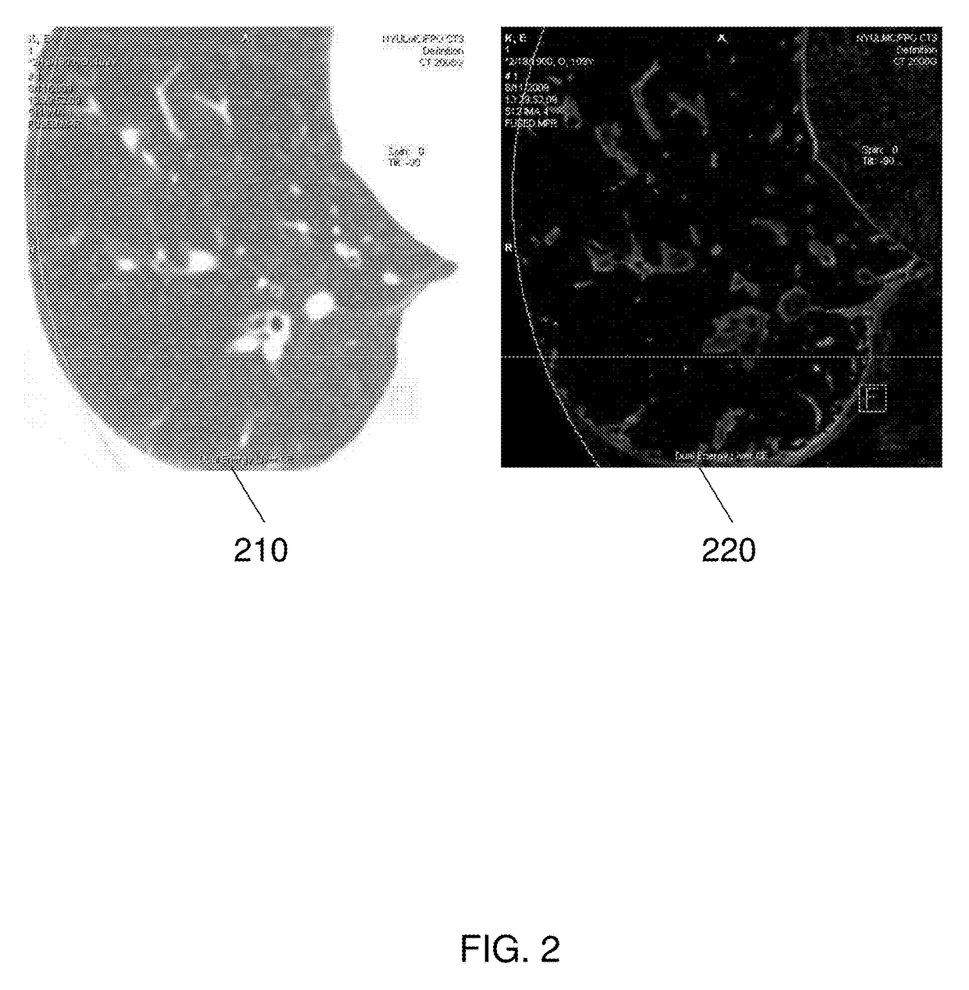
FIG. 2 shows an average energy Computed Tomography (CT) image and a corresponding iodine map computed according to an exemplary embodiment of the present invention.

If a patient has been given iodinated contrast, a "virtual non-contrast" (VNC) volume $V_{vnc}$, and an "iodine map" volume $V_{iodine}$ may be computed. Both of these volumes are derived from the original acquisitions $V_{low}$ and $V_{high}$. The iodine map shows for every voxel, the computed amount of iodine present at the location in the body. The VNC image depicts how the acquisition would have looked without contrast agent, and may be computed by subtracting the iodine map from the post-contrast image. Other methods may also be used for computing the derived volumes $V_{average}$, $V_{vnc}$, and $V_{iodine}$. FIG. 2 shows $V_{average}$ and $V_{iodine}$ for a section of the lungs in one patient. More particularly, the left image 210 of FIG. 2 shows an average energy $V_{average}$ and the right image 220 of FIG. 2 shows a corresponding iodine map $V_{iodine}$. The bright values (e.g., the mostly non-black areas) in $V_{iodine}$ show areas of increased iodine uptake.

Included in the method for simultaneously estimating the density of airway walls without contrast and the density increase following iodine administration, is a step of segmenting the airway lumen from CT volumes in order to determine the locations of the airway walls 120 (see FIG. 1).

For example, the bronchial tree is segmented throughout the lungs from one of the CT volumes $V_{average}$, $V_{low}$, and $V_{high}$. A variety of airway segmentation methods from CT may be used such as those described in: Kiraly A. P., McLennan G., Hoffman E. A., Reinhardt J. M., and Higgins W. E., "Three-dimensional human airway segmentation methods for clinical virtual bronchoscopy", *Academic Radiology*, 2002. 9 (10): p. 1153-1168; Fetita C. I., Preteux F., Beigelman-Aubry C., and Grenier P., (2004) "Pulmonary airways: 3-D reconstruction from multislice CT and clinical investigation," vol. 23, no. 11, *IEEE Trans. Medical Imaging*, Nov. 2004; Kiraly A. P., Helferty J. P., Hoffman E. A., McLennan G., and Higgins W. E., "Three-Dimensional Path Planning for Virtual Bronchoscopy", In *IEEE Transactions on Medical Imaging*, vol. 23, no. 1, November 2004: p. 1365-1379, the disclosures of which are incorporated by reference herein in their entireties.

This segmentation may be further refined to segment the airway walls. A variety of airway wall segmentation techniques may be used such as those described in B. Odry, A. P. Kiraly, G. Slabaugh, C. L. Novak, "Active contour approach for accurate quantitative airway analysis", SPIE Medical Imaging 2008, Proceedings of the SPIE Vol. 6916, p. 691613, 2008; and A. P. Kiraly, B. L. Odry, D. P. Naidich, C. L. Novak, "Boundary-Specific Cost Functions for Quantitative Airway Analysis", Medical Image Computing and Computer Assisted Intervention (MICCAI) 2007, p. 784-791, the disclosures of which are incorporated by reference herein in their entireties. In the first method, a cross-section of the identified airway branch is sampled from the original volume and airway walls are segmented by edge-based filters and a minimum energy path is computed through the edges. Alternatively, the airway wall may be segmented locally based on a user's click as described in U.S. Patent Application Publication No. 20120268450 entitled "Automated Detection of Airway and Vessel Orientations for Quantitative Analysis and Visualization," the disclosure of which is incorporated by reference herein in its entirety.

The input to these segmentation methods may be one of the CT volumes $V_{low}$ or $V_{high}$ or the weighted average volume $V_{average}$. The segmentation of either the airway tree or a single airway branch creates an airway wall map $M_{airway}$ that indicates for each voxel in the map, whether it is part of the airway wall or not. In the case where the entire bronchial tree is segmented and modeled into a hierarchical tree as described earlier, voxels that are part of the airway wall may also indicate topological information for each branch, including parent branch and generation number.

Alternatively, the information may be stored in the following way: for each branch in the automatically segmented airway tree, or for a specific branch selected by the user, the information may be included in a list of all the voxels $L_{airway}$ that are in the wall of that branch.

In either storage method, the voxels that form the wall of a given airway branch or a set of branches may be easily retrieved.

Included in the method for simultaneously evaluating the density of airway walls prior to the administration of contrast and the density increase following iodine administration, is a step of computation of dual densities 130 (see FIG. 1).

For example, for each branch or set of branches, a set of locations that form the wall of each branch (from either the map $M_{airway}$ or the list $L_{airway}$) is taken and their values in the Virtual Non-Contrast image $V_{VNC}$ are sampled to estimate the pre-contrast density. Given the set of samples of pre-contrast densities, a value such as the arithmetic mean, median, maximum, etc., is computed to yield a bronchial wall density for each branch b to yield $D_b$.

In addition, for each branch or set of branches, the set of locations that form the wall of each branch (from either the map $M_{airway}$ or the list $L_{airway}$) is taken and their values in the Iodine Map $V_{iodine}$ are sampled to determine the inflammation as measured by the iodine uptake. Given the set of samples of pre-contrast densities, a value such as the arithmetic mean, median, maximum, etc., is computed to yield a bronchial wall uptake for each branch b to yield $I_b$.

Included in the method for simultaneously evaluating the density of airway walls prior to the administration of contrast and the density increase following iodine administration, is a step of utilization of computed wall density and inflammation values 140 (see FIG. 1).

For example, given the Density measures $D_b$ and Inflammation measures $I_b$, these measures can be used to predict patient disease severity, optimal treatment protocol, prognosis, or likely treatment outcome. These features can be used individually, or in combination. Given these features or feature combinations, a scoring system can be developed to quantify disease severity and extent throughout the bronchial tree and track changes in disease severity over time or in response to treatment.

These measures can be automatically computed, using the described or referenced methods, from dual energy CT volumes acquired with contrast and can be utilized to predict disease severity and treatments.

An exemplary embodiment of the present invention provides a method for presentation of airway abnormalities from CT.

As discussed above in the Background section, after a tree model is obtained, an automated method can generate measurements of the airway dimensions, including wall thickness and lumen diameter. An example of this is described in B. Odry, A. P. Kiraly, G. Slabaugh, C. L. Novak, "Active contour approach for accurate quantitative airway analysis", SPIE Medical Imaging 2008, Proceedings of the SPIE Vol. 6916, p. 691613, 2008; and A. P. Kiraly, B. L. Odry, D. P. Naidich, C. L. Novak, "Boundary-Specific Cost Functions for Quantitative Airway Analysis", Medical Image Computing and Computer Assisted Intervention (MICCAI) 2007, p. 784-791. In the first method, a cross-section of the identified airway branch is sampled from the original volume, airway walls are segmented by the edge-based filters and a minimum airway path is computed through the edges. Further details are found in the aforementioned papers. Airway measurements can be classified as normal or abnormal based on expected values from healthy cases.

Subsequently, functional aspects of the airways can be estimated as derivations of measured features or additional ones such as airway wall inflammation, using Dual Energy acquisition, or the presence of mucoid impaction on the bronchi. An example of this is described in B. L. Odry; D. Guiliguian; A. P. Kiraly; C. L. Novak; D. P. Naidich; J F Lerallut, "Automated detection of mucus plugs within bronchial tree in MSCT images" Proc. SPIE 6511 Medical Imaging 2007, 651110, the disclosure of which is incorporated by reference herein in its entirety. The presence of mucoid foci is common in patients with airway disease and usually is the result of infection. Mucoid foci also reduce the airflow throughout the lung with an increasing impact depending on where they are located in the bronchial tree.

The bronchial tree consists of hundreds of individual branches. Current airway modeling algorithms, in addition to depicting branch characteristics and hierarchy, allow classification of branches according to generation and lung lobe. An example of the generation of the airway model is described in Kiraly A. P., Helferty J. P., Hoffman E. A., McLennan G., and Higgins W. E., "Three-Dimensional Path Planning for Virtual Bronchoscopy", In *IEEE Transactions on Medical Imaging*, vol. 23, no. 1, November 2004: p. 1365-1379. Once the model is obtained, the branches can be classified into different lobes by evaluating the final branch locations relative to known lobe locations. This provides an opportunity to assess the performance of a lung or lung region non-invasively by lobe region from a CT volume, and can provide a quick indication where an issue might exist.

In the method for presentation of airway abnormalities from CT, the airflow within the lung may be assessed by using pointers to regions that are impacted. As a result, a radiologist's attention can be directed specifically to abnormal airways/regions, with priority given to the most severe abnormalities.

Figure 3:
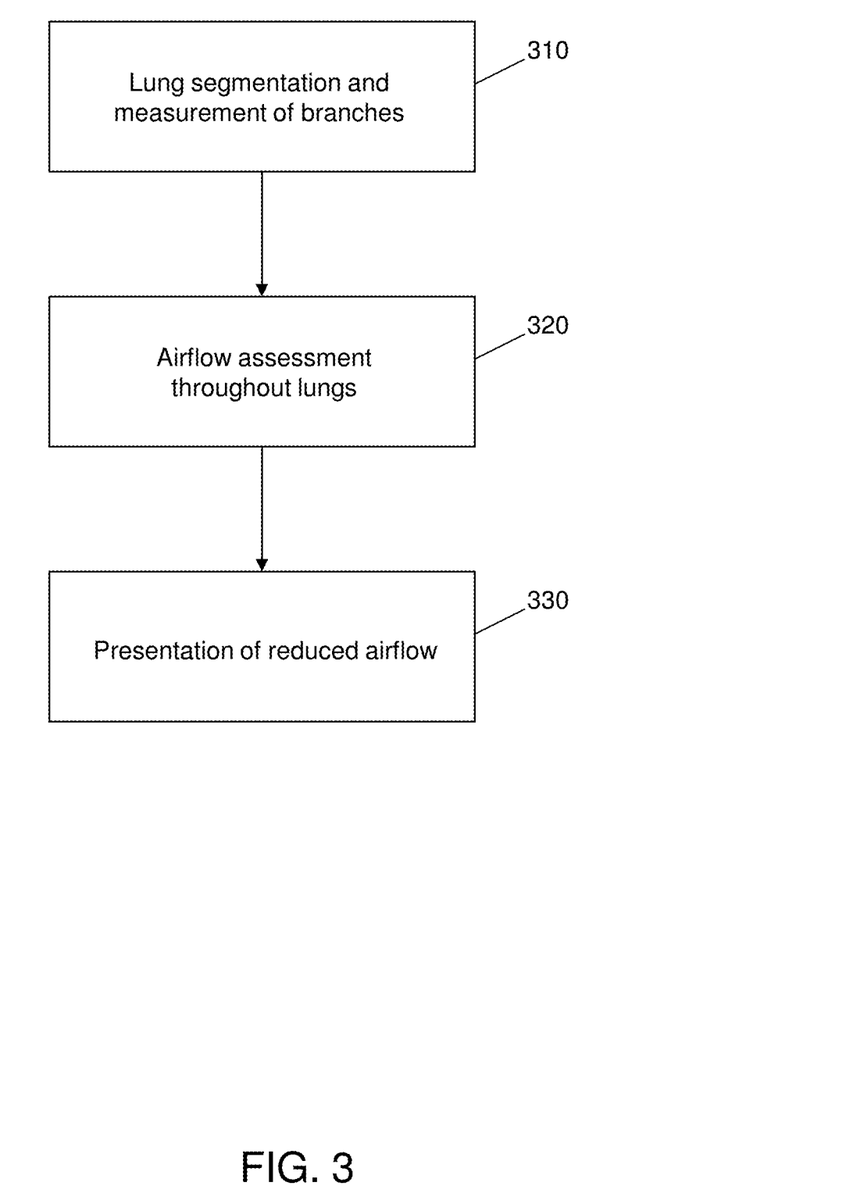
FIG. 3 is a flowchart of a method for presentation of airway abnormalities from CT according to an exemplary embodiment of the present invention.

Included in the method for presentation of airway abnormalities from CT, is a step of lung segmentation and measurement of branches 310 (see FIG. 3).

This method utilizes a model of the bronchial tree extracted from a CT dataset. Several methods may be used to perform this step.

Once the bronchial tree is segmented out, skeletonization and further post-processing may be performed to create a tree model.

After the airway branches have been identified, an automated method may determine the lumen and the wall of each airway. Several methods may be used to compute the lumen and wall extent. These methods yield contours that define the delineation between the lumen and the inner edge of the wall, and between the outer edge of the wall and the surrounding parenchyma.

An automated method for detection of mucoid impactions may be applied using the bronchial tree as well as a lung and lung lobe segmentation technique to obtain volumes of each lung and lobe. An example of this is described in B. L. Odry; D. Guiliguian; A. P. Kiraly; C. L. Novak; D. P. Naidich; J F Lerallut, "Automated detection of mucus plugs within bronchial tree in MSCT images" Proc. SPIE 6511 Medical Imaging 2007, 651110. For lobe segmentation, a method involving a filter to detect ridges and a watershed transform can be used as described in "Lung lobe segmentation by anatomy-guided 3D watershed transform," Jan-Martin Kuhnigk, Horst K. Hahn, Milo Hindennach, Volker Dicken, Stefan Krass, and Heinz-Otto Peitgen, Proceedings of the SPIE, Volume 5032, p. 1482-1490 (2003), the disclosure of which is incorporated by reference herein in its entirety.

Once the voxels that form the lumen have been identified on a given cross section, measurements of the lumen can be derived, such as diameter or area. An abnormal lumen may be too narrow, as in the case of asthma; or too dilated, as in the case of bronchiectasis.

Similarly, once the voxels that form the wall have been identified, measurements of the wall can be derived, including wall thickness and wall area. Typically, abnormal walls are too thick, although theoretically it is possible for a wall to be too thin as well.

In normal patients, the lumen diameter or area varies according to airway generation number, so that there is no single threshold value for lumen diameter (or area) that is an indicator of healthy dimensions. To get around this, many clinical methods for examining airways recommend comparing its size to that of the adjacent artery. In a healthy airway, the diameter of the lumen will be approximately equal to that of the adjacent artery, because they will both decrease in size as generation number increases.

Furthermore, wall width will also decrease as generation number increases in healthy patients. Therefore, one clinical rule is that the wall width should be approximately one-quarter the artery's diameter.

Ratios significantly different from 1.0 in the case of the lumen and significantly different from 0.25 in the case of the wall are indicators of airway disease. The degree of severity is indicated by how much above 1.0 the lumen-to-artery ratio is, and how much above 0.25 the wall-to-artery ratio is.

Included in the method for presentation of airway abnormalities from CT, is a step in which the adjacent artery is automatically detected. As an example, see B L. Odry; A P. Kiraly; C L. Novak; D P. Naidich; J-F Lerallut "Automated airway evaluation system for multi-slice computed tomography using airway lumen diameter, airway wall thickness and broncho-arterial ratio" Proc. SPIE 6143 Medical Imaging 2006, 61430Q. In this case, the diameter (or cross-sectional area) of this automatically detected companion artery is computed to calculate the ratio of the bronchial lumen to artery—the BLA ratio. The ratio of the bronchial wall thickness to the artery diameter—the BWA ratio—is also computed.

Other methods may be used to identify which airways have abnormal measures such as the ratio of Lumen Area to Overall Area (lumen plus wall). Alternatively, lookup tables can be employed to give thresholds or cut-off values for normal versus abnormal lumen and wall sizes for different generation numbers.

Included in the method for presentation of airway abnormalities from CT, is a step of airflow assessment throughout the lungs 320 (see FIG. 3).

Given the above computed features, regions where the airflow will be impacted can be estimated. For example, the airflow could be impacted because of mucoid impactions partially or completely blocking airway ducts, narrowing the airway lumen or thickening the airway walls.

Using the hierarchical structure of the tree, one can detect where in the lung airflow is affected (e.g., lobe) and at which level (e.g., generation). For example, for each generation the number of corresponding child branches is known. For example, the Boyden classification identifies how many airways are available at every generation. Therefore, the extent of airflow reduction based on where the abnormality occurs can be estimated.

With a regular standard dose, sharp kernel CT on a normal patient, most bronchial tree algorithms fully reach the $8^{th}$ generation, wherein the $8^{th}$ generation corresponds to 1860 airway branches. This number could vary based on the acquisition parameters (e.g., dose, reconstruction kernel). In an exemplary embodiment of the present invention, this number of airways is set as the standard N which would correspond to maximum airflow. There is one standard maximum N(i) per lobe, where i is between 1 and 5 for each of the 5 lobes, that is automatically computed beforehand.

Assessment of airflow is done as follows.
1. For mucoid impaction, the generation where mucoid impaction is detected is used to determine the number of children branches that are potentially impacted $N_{impacted}(i)$. An estimated impacted volume $V_{impacted}(i)$ is computed using the ratio between the actual $N_{impacted}(i)$ and N(i).

$$V_{impacted}(i) = V(i) \cdot \frac{N_{impacted}(i)}{N(i)}$$

where V(i) is the total volume of lobe i.
2. In the case of partial blockage with mucoid impactions, a weight K (between 0 and 1) is applied to $V_{reduced}(i)$ according to the percentage of the airway that is blocked.
3. For deficient airway modeling (e.g., wall thickening or re-modeling), the estimation of reduced flow is computed based on the estimated narrowing of the lumen or thickening of the wall (e.g., BLA or BWA ratios). The use of this set of measurements can be used either by:
   3.1. Considering patient airways (e.g., low generation in the hierarchical tree) that present such abnormalities, and the number of children branches. Weight associated to the BLA or BWA ratios applied accordingly produce the impacted volume:

$$V_{impacted}(i) = V(i) \cdot R_{parentAirway} \frac{N_{impacted}(i)}{N(i)},$$

where R could be BLA or BWA ratio based on narrowing or wall thickening.
   3.2. Or consider all airways individually and use associated BLA or BWA ratios in a sum towards N(i). $N_{impacted}(i)$ will then be a sum of all airways with their respective ratios:

$$V_{impacted}(i) = V(i) \cdot \frac{\sum_{j=0}^{N(i)} R_j}{N(i)}.$$

Included in the method for presentation of airway abnormalities from CT, is a step of presenting the reduced airflow 330 (see FIG. 3).

For example, using the lobe and airway segmentation model, the estimated impacted volume could be projected, starting from an impacted parent airway and following the contours of what is/would be the airway tree beyond this starting branch. The impacted branch, which is the start point, can be restricted due to mucoid foci, lumen narrowing or wall thickening.

Color coding can be used to depict the percentage of impacted volume compared to the total computed lobe volume. This percentage can be associated with a scoring system to map percentages to different colors that would give a quick indication to the user that there are abnormalities of a particular extent and severity. One such mapping could be: Red—severely abnormal, Orange—moderately abnormal, Yellow—mildly abnormal, Green—normal. Other mappings are possible.

This result would make it easier for physicians to assess airway disease and ensure significant problems are not missed.

An exemplary embodiment of the present invention provides a method for reduction of partial volume effects for visualization of iodine in airway walls.

As discussed above in the Background section, one result of DECT imaging is an iodine map that depicts the amount of iodine uptake at any given location in the volume. The iodine map can be shown as a colored overlay on top of the gray-scale CT image to indicate greater or lesser amounts of iodine.

However, the iodine map shows not only contrast in the airway walls, but also in the pulmonary vessels—both arteries and veins.

Figure 4:
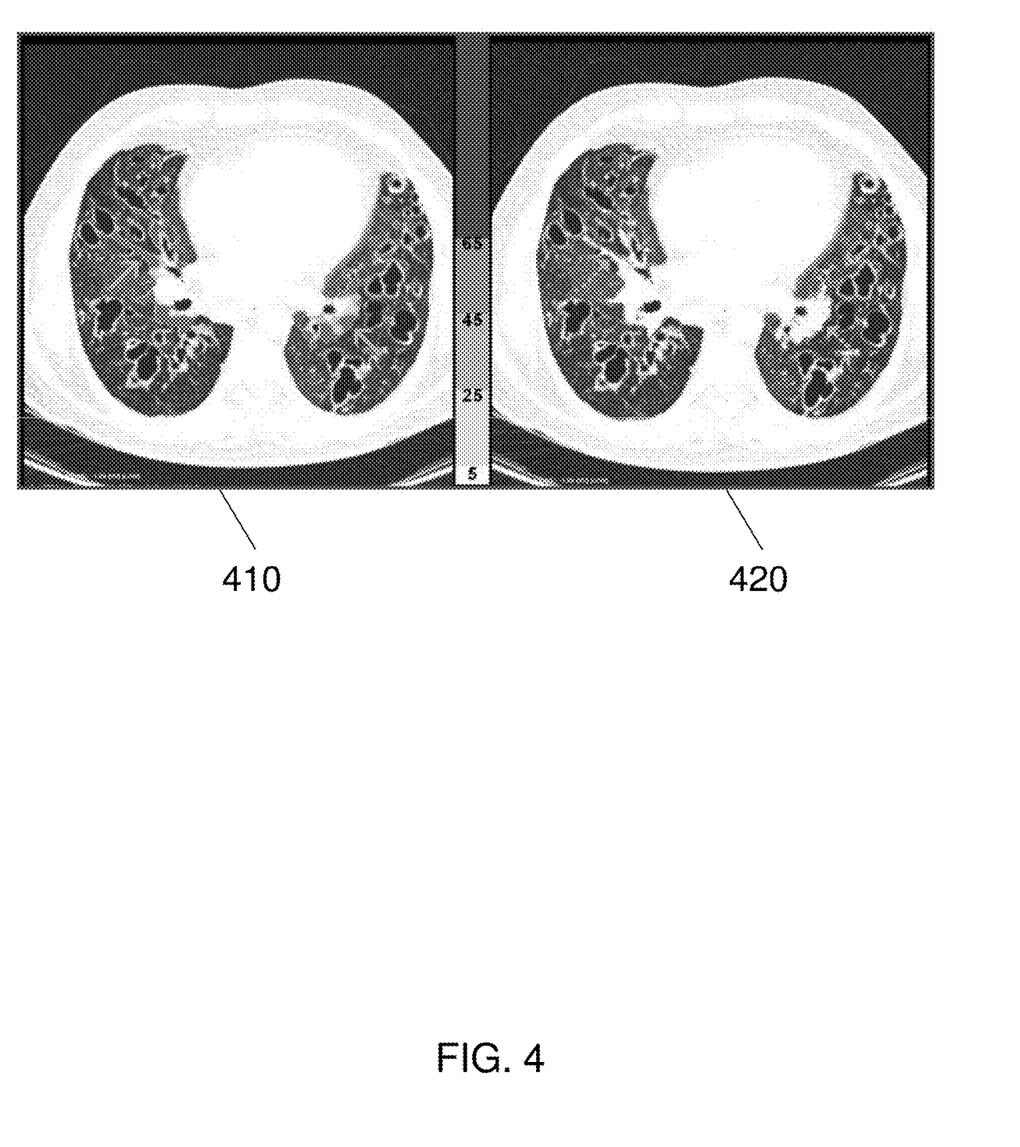
FIG. 4 is a CT image of the lungs overlaid with an iodine map before and after masking of major pulmonary vessels.

It is possible to set a threshold to suppress the display of much of the iodine in vessels. Even with iodine, airway walls exhibit CT values well below 0 Hounsfield Units (HU). Therefore, one may modify the overlay display in multi-planer reconstructions (MPRs) to not show any color when the CT value in the low energy CT volume is 0 HU or greater. The result before and after is shown in FIG. 4. The arrows point to specific large vessels where the iodine overlay has been shown (left) or not (right).

FIG. 4 is a CT image of the lungs overlaid with an iodine map before and after masking of major pulmonary vessels. The iodine map is shown as a color overlay ranging from no color (0 to 5 HU) through yellow (5 to 25 HU) to red (65 HU and greater).

The left side 410 of FIG. 4 shows the overlay before thresholding, while the right side 420 of FIG. 4 depicts the result of using 0 HU as a threshold to suppress large vessels from exhibiting the iodine. Large vessels appear completely red in the left image 410 (solid arrows) where the iodine overlay is rendered, and mostly white in the right image 420 when the overlay is suppressed (dotted arrows). However, a red rim remains around the edges of large vessels.

In other words, even after thresholding, there still remains a "rim" of iodine visualized at the edges of vessels, due to partial volume effect.

In the method for reduction of partial volume effects for visualization of iodine in airway walls, the visualization of the iodine in vessels throughout the lungs is explicitly suppressed, while leaving the visualization in airway walls. This method is completely automatic and does not rely on any user interaction to select specific vessels. The result is a visualization of the inflammation map throughout the thoracic region, but without distracting vessels highlighted and without the partial volume effects that are possibly confusing to the user. This makes it easier for radiologists to focus on contrast uptake in the airway walls.

Figure 5:
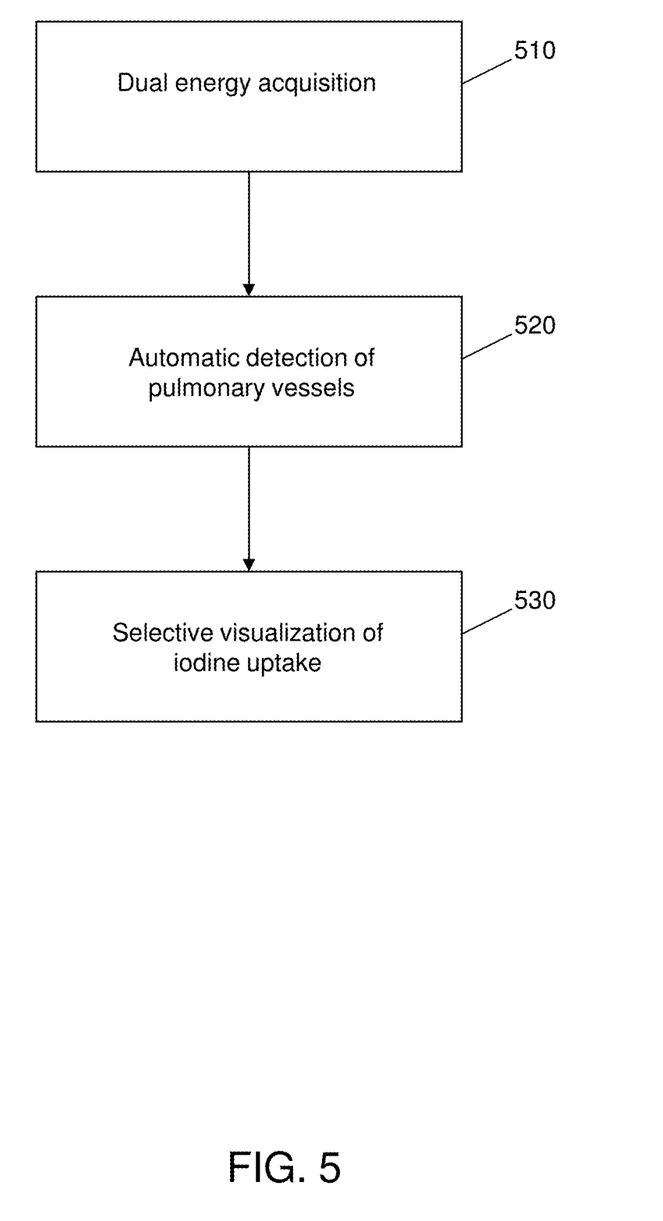
FIG. 5 is a flowchart of a method for masking vessels for improved visualization of iodine in airway walls according to an exemplary embodiment of the present invention.

Included in the method for reduction of partial volume effects for visualization of iodine in airway walls, is a step of dual energy acquisition 510 (see FIG. 5).

As described above in the method for simultaneously evaluating the density of airway walls prior to the administration of contrast and the density increase following iodine administration, a dual energy acquisition may produce two volumes, one at low energy (e.g., 80 kV) and one at high energy (e.g., 140 kV). These volumes may be referred to as $V_{low}$ and $V_{high}$. A computer with a Dual Energy software module may be used to create a volume that simulates an acquisition at an average energy $V_{average}$ (e.g., 120 kV), by taking a weighted average of $V_{low}$ and $V_{high}$.

If a patient has been given iodinated contrast, a "virtual non-contrast" (VNC) volume $V_{vnc}$, and an "iodine map" volume $V_{iodine}$ may be created. Both of these volumes are derived from the original acquisitions $V_{low}$ and $V_{high}$. The iodine map shows for every voxel, the computed amount of iodine present at the location in the body. The VNC image depicts how the acquisition would have looked without contrast agent, and may be computed by subtracting the iodine map from the post-contrast image. Other methods may also be used for computing the derived volumes $V_{average}$, $V_{vnc}$, and $V_{iodine}$.

Included in the method for reduction of partial volume effects for visualization of iodine in airway walls, is a step of automatic detection of pulmonary vessels 520 (see FIG. 5).

Several methods may be used to perform automatic segmentation of pulmonary vessels from a CT volume. In the case of dual energy CT, the segmentation may be performed using the average image $V_{average}$ or the low or high energy volumes $V_{low}$ or $V_{high}$. The result of an automatic vessel segmentation is a volume map S, wherein each voxel in the original CT volume has a 1 if the voxel lies within a vessel or a 0 if not. The vessel segmentation procedure may be modified to perform extra dilation steps to ensure that the edges of the vessels are captured in the map S, thus further reducing partial volume effects.

A map $S_{not}$ that indicates voxels that do not have vessels may be computed, by taking the logical "not" of S. Taking the logical "and" of $S_{not}$ and $V_{iodine}$ can yield a map of iodine outside the vessels $I_{nv}$.

The map $S_{not}$ can be further modified by taking the logical "or" with the map of airway wall locations. In this way, voxels at the edge of the vessels that impinge upon the edge of an airway wall can be restored to the map $S_{not}$ prior to computing the map of iodine in non-vessel locations $I_{nv}$.

Included in the method for reduction of partial volume effects for visualization of iodine in airway walls, is a step of selective visualization of iodine uptake 530 (see FIG. 5).

Given the above computations, MPRs of gray-scale CT data may be visualized with an iodine map overlay. The MPRs may consist of the entire field of view of the chest, whether at orthogonal axes (e.g., axial, sagittal, coronal), or at arbitrary angles. The MPRs may also show local zoomed areas of individual airways, whether at orthogonal axes or arbitrary angles.

The gray scale data in the MPR is interpolated from the $V_{average}$ dataset that depicts a typical CT acquisition at average energy that provides a good trade-off between image contrast and noise. Alternatively, the gray scale data may be interpolated from the $V_{low}$ or $V_{high}$ dataset.

The overlay data is interpolated from the not-vessel iodine map $I_{nv}$ that depicts the amount of iodine uptake in voxels outside the vessels. The overlay may use a color lookup table that depicts differing amounts of iodine as different hues, such as red for large amounts of iodine, yellow for moderate amounts of iodine, and green for little or no iodine. Other color maps may be used. Additionally, the user is provided with a means to control the "alpha blend" to make the overlay colors more or less transparent.

The method for reduction of partial volume effects for visualization of iodine in airway walls described above is a fully automatic method for selectively suppressing the visualization of iodine uptake in pulmonary vessels in DECT images. The method does not require any user input and can be performed off-line so the user does not have to wait for the calculation. The method allows for the reduction of partial volume effects compared with simple thresholding. The result is a visualization with iodine depicted only in the areas of interest to physicians studying iodine uptake in bronchial walls.

An exemplary embodiment of the present invention provides another method for presentation of airway abnormalities from CT.

As discussed above in the Background section, the bronchial tree consists of hundreds of individual branches, each of which may have normal or abnormal dimensions. Given a branch with abnormal dimensions, it may be abnormal in its wall thickness, its lumen diameter or both. The degree of abnormality may vary from one branch to another.

Radiologists typically assess the airways by scrolling systematically through a CT volume, most often by visually inspecting axially oriented slices. To detect and assess abnormalities, they must repeatedly search each slice. However, airways are often not oriented exactly within the scan plane, but instead pass obliquely through it.

In addition, airway walls may be assessed for inflammation as well as for abnormal dimensions, using a procedure for analyzing DECT. As mentioned above, the airway walls in patients with airway disease experience an increase in apparent density following the administration of iodinated contrast, and that the uptake may be correlated with airway inflammation.

The degree of iodine uptake of inflammation can also be quantified or visualized, just like the airway dimensions. However, the radiologist may not be able to determine where the greatest amount of inflammation is due to the myriad of airway branches.

The current method for presentation of airway abnormalities from CT provides a way to direct the radiologist's attention specifically to abnormal airways, with primary attention given to the most severe abnormalities.

Figure 6:
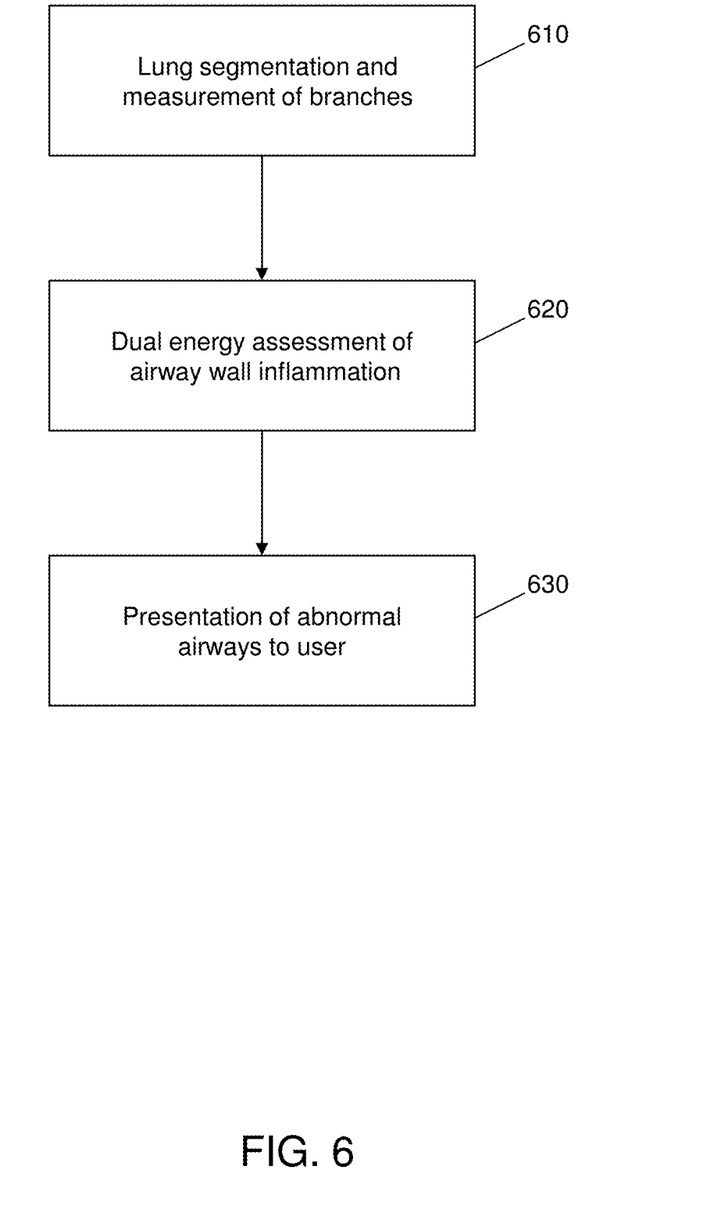
FIG. 6 is a flowchart of a method for presentation of airway abnormalities from CT according to an exemplary embodiment of the present invention.

Included in the method for presentation of airway abnormalities from CT, is a step of lung segmentation and measurement of branches 610 (see FIG. 6). This step is substantially the same as the step of lung segmentation and measurement of branches discussed above for the first method of presentation of airway abnormalities from CT. Accordingly, a repeated description is not provided.

Included in the method for presentation of airway abnormalities from CT, is a step of dual energy assessment of airway and wall inflammation 620 (see FIG. 6).

As described above for the method of for simultaneously evaluating the density of airway walls prior to the administration of contrast and the density increase following iodine administration, a dual energy acquisition may produce two volumes, one at low energy (e.g., 80 kV) and one at high energy (e.g., 140 kV). These volumes may be referred to as $V_{low}$ and $V_{high}$. A computer with a Dual Energy software module may be used to create a volume that simulates an acquisition at an average energy $V_{average}$ (e.g., 120 kV), by taking a weighted average of $V_{low}$ and $V_{high}$.

If a patient has been given iodinated contrast, a "virtual non-contrast" (VNC) volume $V_{vnc}$, and an "iodine map" volume $V_{iodine}$ may be created. Both of these volumes are derived from the original acquisitions $V_{low}$ and $V_{high}$. The iodine map shows for every voxel, the computed amount of iodine present at the location in the body. The VNC image depicts how the acquisition would have looked without contrast agent, and may be computed by subtracting the iodine map from the post-contrast image. Other methods may also be used for computing the derived volumes $V_{average}$, $V_{vnc}$, and $V_{iodine}$.

Given the automatic airway segmentation, the iodine uptake in the wall of each branch is computed. This can be done by utilizing all the voxels that fall between the inner and outer wall contours. The values of the voxels are determined from the iodine map $V_{iodine}$. The values may be averaged, or alternatively the maximum, median or another function may be utilized.

The result is an estimate of the iodine uptake (for each branch of the bronchial tree) which can be used as a proxy for degree of inflammation.

Included in the method for presentation of airway abnormalities from CT, is a step of presentation of abnormal airways to a user 630 (see FIG. 6).

Given BLA and BWA ratios for each individual branch in the bronchial tree, they can be ordered from most to least severely abnormal by sorting from highest to lowest BLA and highest to lowest BWA.

Alternatively if ratios are used, the lumen diameter (or area) can be sorted first by generation number and then by size. For example, this may start from the $4^{th}$ or $5^{th}$ generation. This will yield a list of $4^{th}$ generation airways from most to least abnormal, then $5^{th}$ generation airways from most to least abnormal, etc.

Similarly, if the BWA ratio is not available, the wall thicknesses can be sorted by generation and then by wall thickness.

The inflammation values from the iodine map can also be sorted from most uptake to least uptake.

The user may indicate a desire to see abnormal branches and then be shown the most abnormal branch according to selected criteria of lumen size, wall size or wall inflammation.

The display may include a magnified view of the most abnormal airway with an MPR reconstruction that is exactly perpendicular to the airway's axis to show the airway's cross-section. The inner and outer wall contours can also be overlaid on the display to show the user how the abnormality was computed. If the ratio with the adjacent artery is utilized, the contour defining the artery size is also shown.

The display may also show an MPR that is oriented with the airway's axis (rather than perpendicular to it) and exactly through the center.

In addition, the display may include a separate window with an axial, coronal and sagittal view of the entire chest to give the context of where the airway is located within the chest.

Upon selecting "next" or using arrow keys or other means, the user is then shown the next more abnormal airway. This process is repeated as often as the user wishes, or until there are no more abnormal airways to be shown.

The method for presentation of airway abnormalities from CT described above automatically assesses the myriad airway branches within a patient's bronchial tree, and selects which ones to present to a user, and the order in which they should be presented. This makes it easier for physicians to assess airway disease and ensure they did not miss significant problems.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article or manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 7:
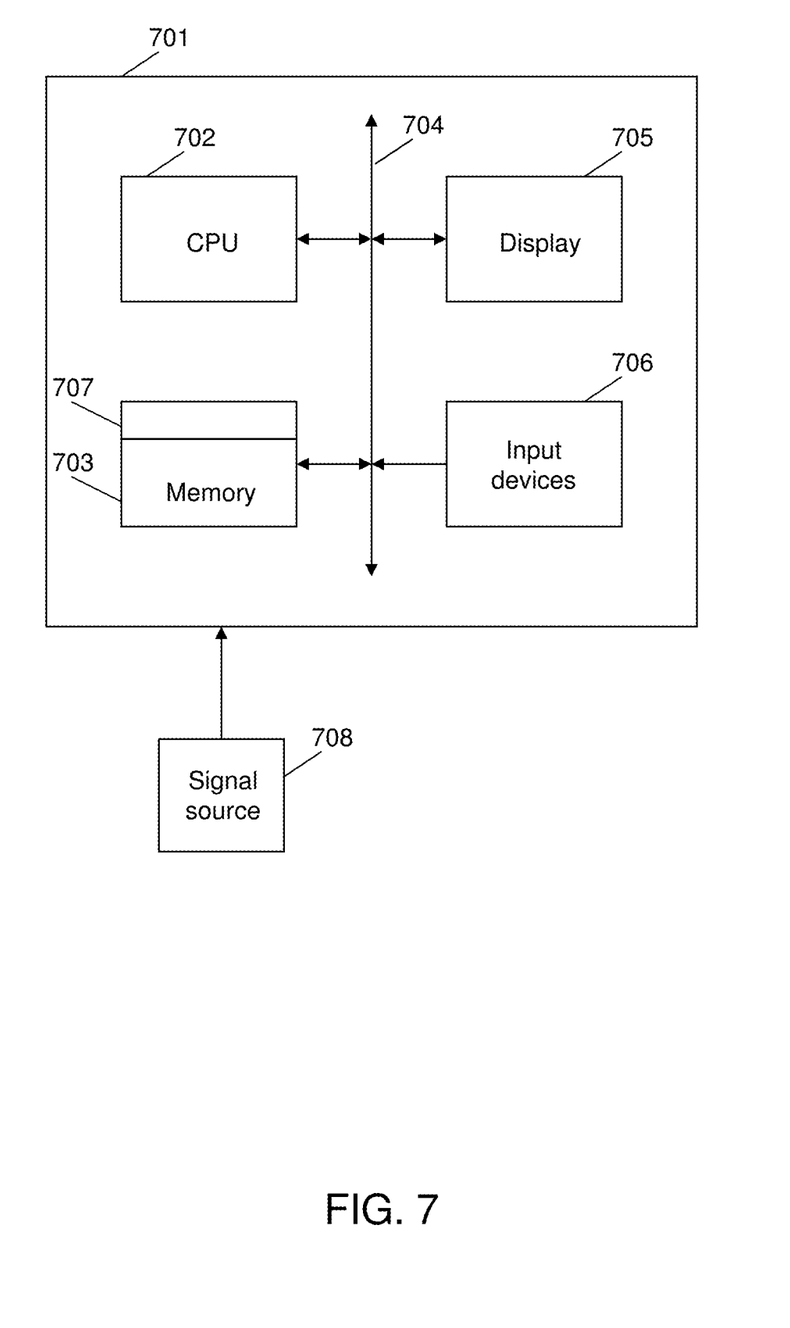
FIG. 7 is a computer system in which an exemplary embodiment of the present invention may be implemented.

Referring now to FIG. 7, according to an exemplary embodiment of the present invention, a computer system 701 can comprise, inter alia, a central processing unit (CPU) 702, a memory 703 and an input/output (I/O) interface 704. The computer system 701 is generally coupled through the I/O interface 704 to a display 705 and various input devices 706 such as a mouse and keyboard. The support circuits can include circuits such as cache, power supplies, clock circuits, and a communications bus. The memory 703 can include RAM, ROM, disk drive, tape drive, etc., or a combination thereof. Exemplary embodiments of present invention may be implemented as a routine 707 stored in memory 703 (e.g., a non-transitory computer-readable storage medium) and executed by the CPU 702 to process the signal from a signal source 708. As such, the computer system 701 is a general-purpose computer system that becomes a specific purpose computer system when executing the routine 707 of the present invention.

The computer system 701 also includes an operating system and micro-instruction code. The various processes and functions described herein may either be part of the micro-instruction code or part of the application program (or a combination thereof) which is executed via the operating system. In addition, various other peripheral devices may be connected to the computer system 701 such as an additional data storage device and a printing device.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described to best explain the principles of the invention and the practical application, and to enable others of ordinary skill in the art to understand the invention for various embodiments with various modifications as are suited to the particular use contemplated.

What is claimed is:

1. A method of evaluating airway wall density, the method comprising:
    providing executable instructions to a processor that when executed by the processor cause the processor to perform the steps of:
    acquiring a simultaneous dual-energy image data of at least a portion of a patient's airway after injection of a contract agent into the patient;
    segmenting a bronchial tree into a branch or a set of branches, from the dual-energy image data to create an airway wall map that indicates for each element in the airway wall map whether it is part of an airway or not;
    computing a virtual non-contrast agent volume map and a contrast agent volume map from the dual-energy image data;
    for each branch or each set of branches, taking a set of locations that form the wall of the airway wall map;
    sampling a value in the virtual non-contrast agent volume map representing a second set of locations corresponding to at least a portion of the set of locations;
    determining a pre-contrast density at each sampled value;
    computing a first bronchial wall density for each branch or each set of branches to yield density measures;
    for each branch or each set of branches, sampling a value in the contrast agent volume map at the second set of locations;
    determining a set of contrast agent intake samples from the contract agent volume sampled values;

computing a value to yield a bronchial wall uptake for each branch or each set of branches to yield inflammation measures; and determining one or more of patient disease severity, optimal treatment protocol, and prognosis using the density measures and inflammation.

2. The method of claim 1, showing for each voxel of the contrast agent volume map a computed amount of contrast agent present at a corresponding location in the patient's body.

3. The method of claim 1, further comprising visualizing wall density or inflammation in a rendering of the bronchial tree.

4. The method of claim 3, wherein the wall density or inflammation is color coded on the rendered bronchial tree.

5. The method of claim 1, wherein the contrast agent includes iodine.

6. A system for evaluating airway wall density, the system comprising:

a central processor unit including a processor in communication with a memory and an input/output interface;

the memory including executable instructions that when executed by the processor cause the processor to perform a method comprising:

acquiring a simultaneous dual-energy image data of at least a portion of a patient's airway after injection of a contract agent into the patient;

segmenting a bronchial tree into a branch or a set of branches, from the dual-energy image data to create an airway wall map that indicates for each element in the airway wall map whether it is part of an airway or not;

computing a virtual non-contrast agent volume map and a contrast agent volume map from the dual-energy image data;

for each branch or each set of branches, taking a set of locations that form the wall of the airway wall map;

sampling a value in the virtual non-contrast agent volume map representing a second set of locations corresponding to at least a portion of the set of locations;

determining a pre-contrast density at each sampled value;

computing a first bronchial wall density for each branch or each set of branches to yield density measures;

for each branch or each set of branches, sampling a value in the contrast agent volume map at the second set of locations;

determining a set of contrast agent intake samples from the contract agent volume sampled values;

computing a value to yield a bronchial wall uptake for each branch or each set of branches to yield inflammation measures; and determining one or more of patient disease severity, optimal treatment protocol, and prognosis using the density measures and inflammation.

7. The system of claim 6, the executable instructions causing the processor to include in each voxel of the contrast agent volume map, a computed amount of contrast agent present at a corresponding location in the patient's body.

8. The system of claim 6, the executable instructions causing the processor to visualize wall density or inflammation in a rendering of the bronchial tree.

9. The system of claim 6, the executable instructions causing the processor to color code the wall density or inflammation on the rendered bronchial tree.

* * * * *